US005114076A

United States Patent [19]

Imai et al.

[11] Patent Number: 5,114,076

[45] Date of Patent: May 19, 1992

[54] ATOMIZER FOR FORMING A THIN FILM

[75] Inventors: Mizuho Imai; Atsuo Ito; Mikio Sekiguchi; Hideyo Iida; Kikuji Fukai; Komei Kato, all of Tokyo, Japan

[73] Assignee: Taiyo Yuden Co., Ltd., Tokyo, Japan

[21] Appl. No.: 726,622

[22] Filed: Jun. 27, 1991

Related U.S. Application Data

[63] Continuation-in-part of Ser. No. 543,166, Jun. 25, 1990, abandoned.

[30] Foreign Application Priority Data

Jun. 30, 1989 [JP] Japan ........ 1-170492
Jun. 30, 1989 [JP] Japan ........ 1-170493

[51] Int. Cl.[5] ........ A61M 11/00
[52] U.S. Cl. ........ 239/338; 239/124; 239/590; 239/590.5; 261/DIG. 65
[58] Field of Search ........ 239/338, 398, 432, 590, 239/124, 597, 601, 590.3, 590.5; 261/DIG. 65, 78.2

[56] References Cited

U.S. PATENT DOCUMENTS

| | | | |
|---|---|---|---|
| 2,709,577 | 5/1955 | Pohndorf et al. | 261/DIG. 65 |
| 3,097,645 | 7/1963 | Lester | 239/338 |
| 3,404,843 | 10/1968 | Szekely | 239/338 |
| 3,759,444 | 9/1973 | Tanaka | 239/338 |
| 4,007,238 | 2/1977 | Glenn | 239/338 |
| 4,116,387 | 9/1978 | Kremer, Jr. et al. | 261/DIG. 65 |
| 4,792,097 | 12/1988 | Kremer, Jr. et al. | 239/432 |

FOREIGN PATENT DOCUMENTS

| | | | |
|---|---|---|---|
| 513052 | 10/1928 | Fed. Rep. of Germany | 239/338 |
| 1951812 | 4/1971 | Fed. Rep. of Germany . | |
| 1536539 | 7/1968 | France | 239/338 |
| 2291800 | 6/1976 | France . | |
| 2573985 | 6/1986 | France | 261/DIG. 65 |

*Primary Examiner*—Andres Kashnikow
*Assistant Examiner*—Christopher G. Trainor
*Attorney, Agent, or Firm*—Flynn, Thiel, Boutell & Tanis

[57] ABSTRACT

An atomizer for forming a thin film comprising an atomizing box, a guide tube having an open end of small diameter and an other open end of large diameter, a nozzle having an ejection outlet disposed in the atomizing box, an atomizing solution reservoir defined in the atomizing box adjacent to the open end of large diameter of the guide tube, and a fluid return passage defined around the circumference of the guide tube for returning the atomized solution from the atomizing solution reservoir to the one open end thereof. The atomizing box can contain a plurality of guide tubes each provided with a nozzle. The guide tube can also have a plurality of nozzles positioned therein.

10 Claims, 6 Drawing Sheets

ATOMIZER FOR FORMING A THIN FILM

This application is a continuation-in-part of U.S. Ser. No. 07/543,166, filed Jun. 25, 1990 now abandoned.

BACKGROUND OF THE INVENTION

1. Field of the Invention

The present invention relates to an atomizer for atomizing a solution of a material and feeding the resultant atomized solution into a film formation chamber where the atomized solution contacts a heated substrate to form the thin film on the surface of the substrate.

2. Prior Art

The conventional atomizers comprise a nozzle in a wind tunnel for atomizing an atomizing solution of a material, a blower provided at a rear side of the nozzle for feeding the atomized solution, a feeding device for receiving the atomized solution and feeding the atomized solution to a film formation chamber.

The conventional film forming device has a problem in that the atomized solution fed from the feeding device shows a wide variety in the diameter of the particles thereof, and has many coarse particles. If the atomized solution colliding with the surface of the substrate has many coarse particles, the thickness and quality of the film formed on the substrate is liable to be locally uneven. That is, it is important that the atomized solution colliding with the surface of the substrate has as many fine particles as possible for forming a thin film having a uniform thickness and quality.

SUMMARY OF THE INVENTION

The present invention is made to solve the problems of the conventional thin film forming device. Hence, it is an object of the present invention is to provide an atomizer for forming a thin film capable of feeding an atomized solution having only fine particles.

To achieve the above object, the atomizer for forming the thin film comprises an atomizing box, a guide tube having an open end of small diameter and an open end of large diameter, a nozzle having an ejection outlet disposed in the atomizing box and directed from the open end of small diameter to the open end of large diameter respectively of the guide tube, an atomizing solution reservoir defined in the atomizing box and confronting the open end of large diameter of the guide tube, an atomized solution discharger connected to said atomizing solution reservoir, and a fluid return passage defined around the circumference of the guide tube, extending from one open end to the other open end thereof for returning the atomized solution from the atomizing solution reservoir to the open end of small diameter.

The above and other objects, features and advantages of the present invention will become more apparent from the following description taken in conjuction with the accompanying drawings.

PREFERRED EMBODIMENTS OF THE INVENTION

FIRST EMBODIMENT (FIGS. 1 AND 2)

Figure 1:
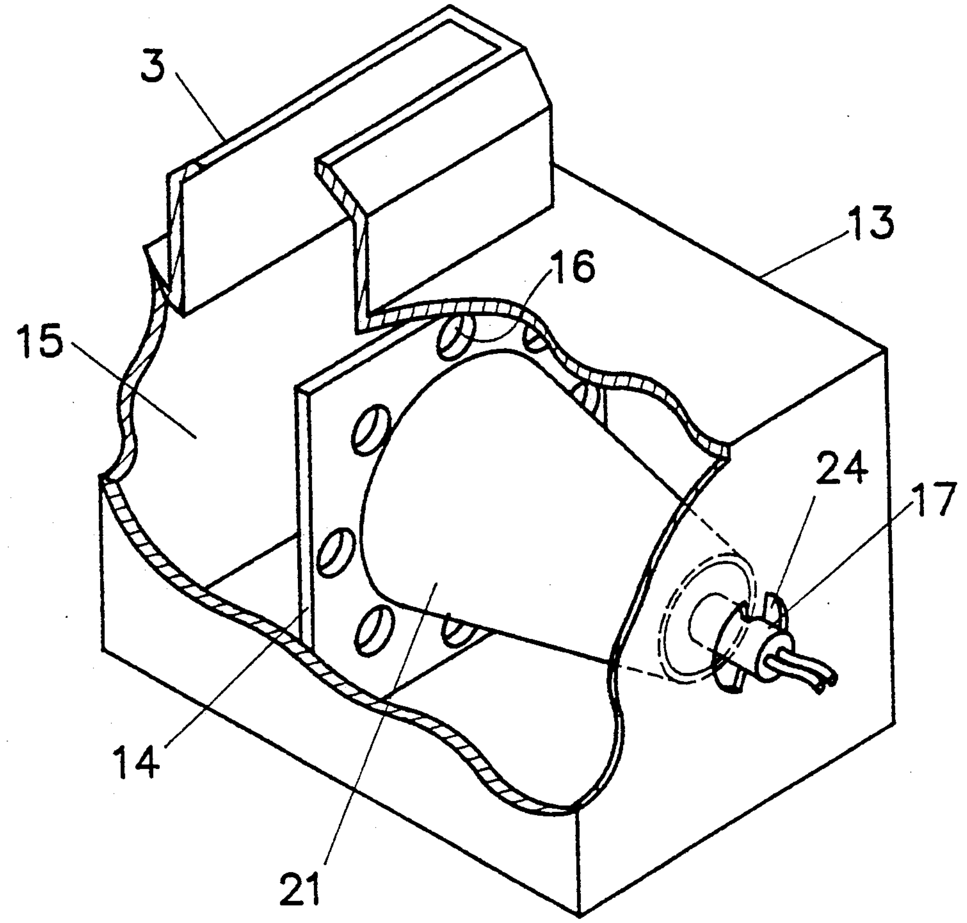
FIG. 1 is a perspective view showing partly cutaway atomizer for forming a thin film according to a first embodiment of the present invention.

An atomizer for forming a thin film (hereinafter referred to as atomizer) includes an atomizing box 13 of a cube shape which has one side surface provided with a through hole 24. The atomizing box 13 has a guide tube 21 which is disposed therein and is tapered to increase its inner diameter from an open end facing the through hole 24 to another open end. A nozzle 17 is inserted into the atomizing box 13 from the through hole 24 and has an ejection outlet positioned in the atomizing box 13 and is directed from the open end of small diameter of the guide tube 21 to the open end of large diameter of the guide tube 21. A solution is sprayed so as to be dispersed as atomized particles in the pressurized air. The thus sprayed atomized particles are also sprayed toward the open end of large diameter of the guide tube 21.

The guide tube 21 has a partition of a handguard shape at the periphery of the open end of large diameter for partitioning the atomizing box 13 perpendicularly. The partition 14 supports the guide tube 21 in the atomizing box 13 and defines an atomized solution reservoir 15 in the atomizing box 13 at the side of the open end of large diameter of the guide tube 21. The partition 14 is perforated to provide a plurality of through holes 16 or perforations which are arranged in a manner so as to surround the open end of large diameter of the guide tube 21. A return passage is defined between the atomized solution reservoir 15 and the open end of small diameter of the guide tube 21 via the perforations 16 and the space around the outer periphery of the guide tube 21.

The atomized solution reservoir 15 has a long cylindrical atomized solution discharger 3 which protrudes from an upper wall of the atomized solution reservoir 15. The particles of the atomized solution in the atomized solution reservoir 15 rise from the atomized solution discharger 3 and are fed to a film formation chamber 4 of the thin film forming device.

Figure 2:
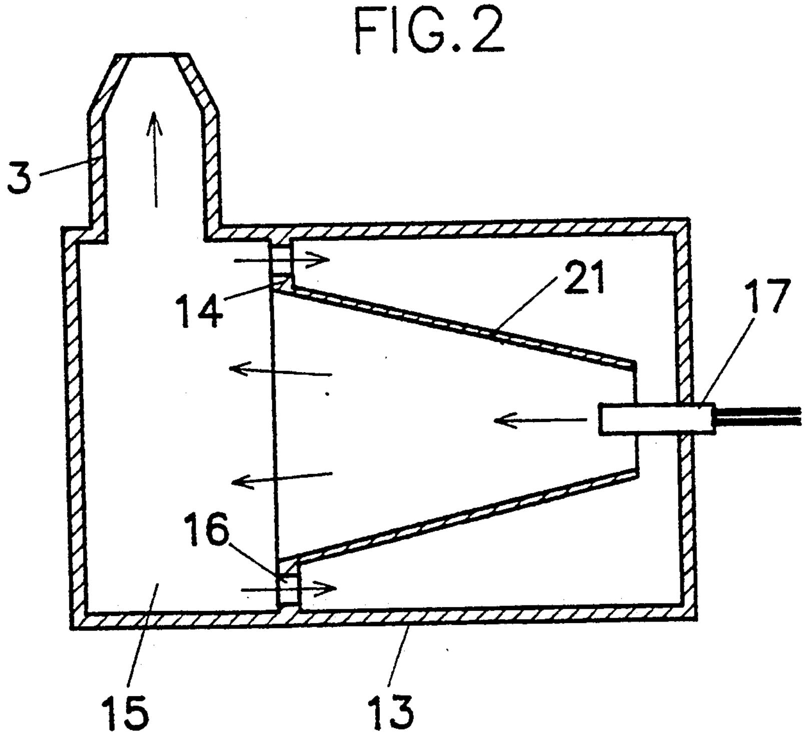
FIG. 2 is a longitudinal cross sectional side view of the atomizer for forming a thin film of FIG. 1.

As illustrated in FIG. 2, when the atomizing solution is sprayed together with the pressurized air from the nozzle 17 attached to the side surface of the atomizing box 13, the atomizing solution is dispersed into the pressurized air in the atomized state and sprayed into the guide tube 21. The atomizing solution thus sprayed in the guide tube 21 spreads and flows toward the atomized solution reservoir 15 through the open end of large diameter. At this time, the particle of the atomized solution are coarse at the peripheral portion adjacent to the guide tube 21 and are dispersed in the periphery of the sprayed route of the atomized solution and adhere to the wall surface of the guide tube 21.

The atomized solution having coarse particles located in the center of the spraying route of the atomized solution is sprayed far away from the fine particles and reaches and collides with the wall surface of the atomized solution reservoir 15 (left side wall in FIG. 2). Hence, the atomized solution having relatively large or coarse particles adhere to the guide tube 21 or the wall surfaces of the atomizing box 13 so that the atomized solution having relatively coarse particles will be changed to liquid drops and eliminated from the floating atomized solution.

The one open end of the guide tube 21 at the side of the nozzle 17 has an area in cross section less than that at the side of the atomized solution reservoir 15, hence the speed of the floating or running fluid is rapid to form a negative pressurized flow. Accordingly, part of the atomized solution in the atomized solution reservoir 15, particularly the particles of the atomized solution collected at the end or the periphery of the atomized solution reservoir 15, is returned to the open end of the small diameter of the guide tube 21 via the space defined circumferentially around the atomizing guide tube 21. The coarse particles of atomized solution thus returned to the nozzle 17 are eliminated from the spraying route so that the fine particles are returned to the atomized solution reservoir 15 and fed upwardly via the atomized solution discharger 3.

Figure 7:
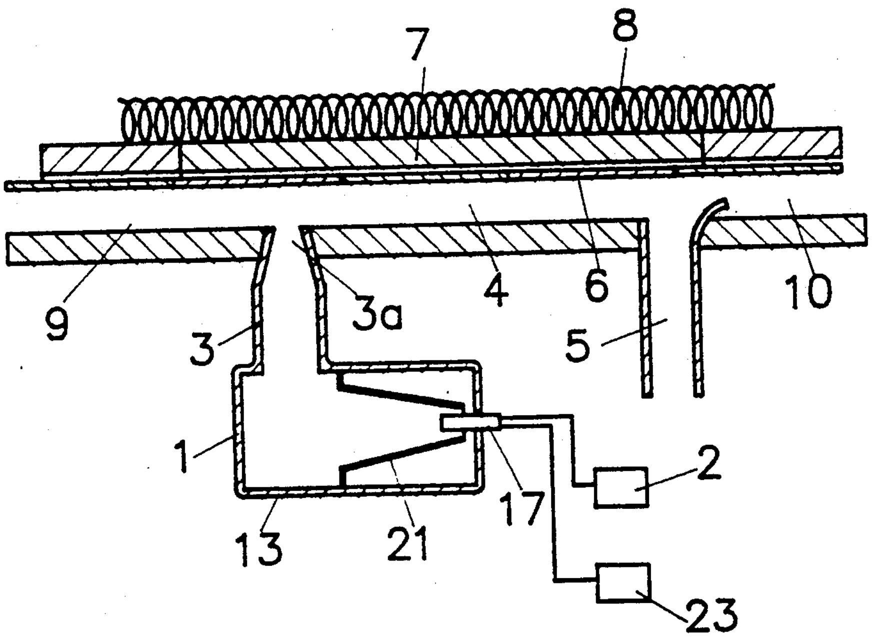
FIG. 7 is a longitudinal cross sectional view of a thin film forming device employing the atomizer.

A schematic arrangement of the thin film forming device employing the atomizer will be illustrated in FIG. 7. In the thin film forming device, the atomizing solution of a material for forming the thin film and a carrier gas (air in most cases) are fed from a solution supply source 23 and an air supply device 2 to the nozzle 17 wherein the atomizing solution is sprayed and discharged from an outlet 3*a* of the atomized solution discharger 3. A film formation chamber 4 is provided over the outlet 3*a* of the atomized solution discharger 3 in which the atomized solution is discharged. There are provided substrates 6, such as glass plates and the like, which form a ceiling of the film formation chamber 4 so as to be successively continuing over the film formation chamber 4 and fed from the left side to the right side in FIG. 7 while it is kept in the film formation chamber 4. The substrates 6 are heated to a predetermined temperature by a heater 8 provided at the rear side thereof via a uniform heating plate 7. The substrates 6 enter from a substrate entrance 9 and successively are fed and discharged from a substrate outlet 10 via the film formation chamber 4.

In the film formation chamber 4 there is provided an outlet 3*a* of the atomized solution discharger 3 at the lower surface of the film formation chamber 4 which is directed from the lower side to the upper side thereof. The atomized solution discharged from the outlet 3*a* floats gently in the film formation chamber 4 in the direction of an outlet 5 provided adjacent to the substrate outlet while contacting the surfaces of the substrates 6. The atomized solution reacts which oxygen in the air or liquid in the atomized solution so that an oxidized thin film forms on the surface of the substrates 6. The atomized solution which does not contribute to form the thin film oxide on the surfaces of the substrates 6 are discharged from the outlet 5.

The atomizer for forming a thin film according to the present invention will be described more in detail with reference to examples thereof.

The atomizing box 13 is a cube-shaped container having a length of 1.3 m, height of 80 cm and width of 80 cm and is provided with a nozzle 17 at one side surface thereof (right side surface in the figures). The nozzle 17 can spray gas fluid and liquid fluid from the ejection outlet at the same time, both of which are atomized. In this case, the two fluids are sprayed under an air pressure of 5 $kg/cm^2$. A chloride solution of Sn and In are employed as the atomizing solution and sprayed under a liquid pressure of 0.2 $kg/cm^2$ for a liquid volume of 4 l/h. As a result, most of the particle of the atomized solution discharged from the atomized solution discharger 3, toward the upper portion thereof, are minute and uniform with a diameter less than 10 $m\mu$ after five minutes has elapsed after the atomizing solution was spray from the ejection outlet of the nozzle 17.

MODIFIED EXAMPLE

There is employed, for forming the atomized solution, a thin film forming device having substantially the same arrangement as the first embodiment except that the guide tube 21 is not provided so that the return flow passage is not defined. The atomized solution discharged from the outlet has atomized particles of a diameter of more than 10 $m\mu$. This is caused by so called knocking at the spraying port of the nozzle 17 due to the large variation of the pressure in the atomizing box 13.

SECOND EMBODIMENT (FIGS. 3 AND 4)

Figure 3:
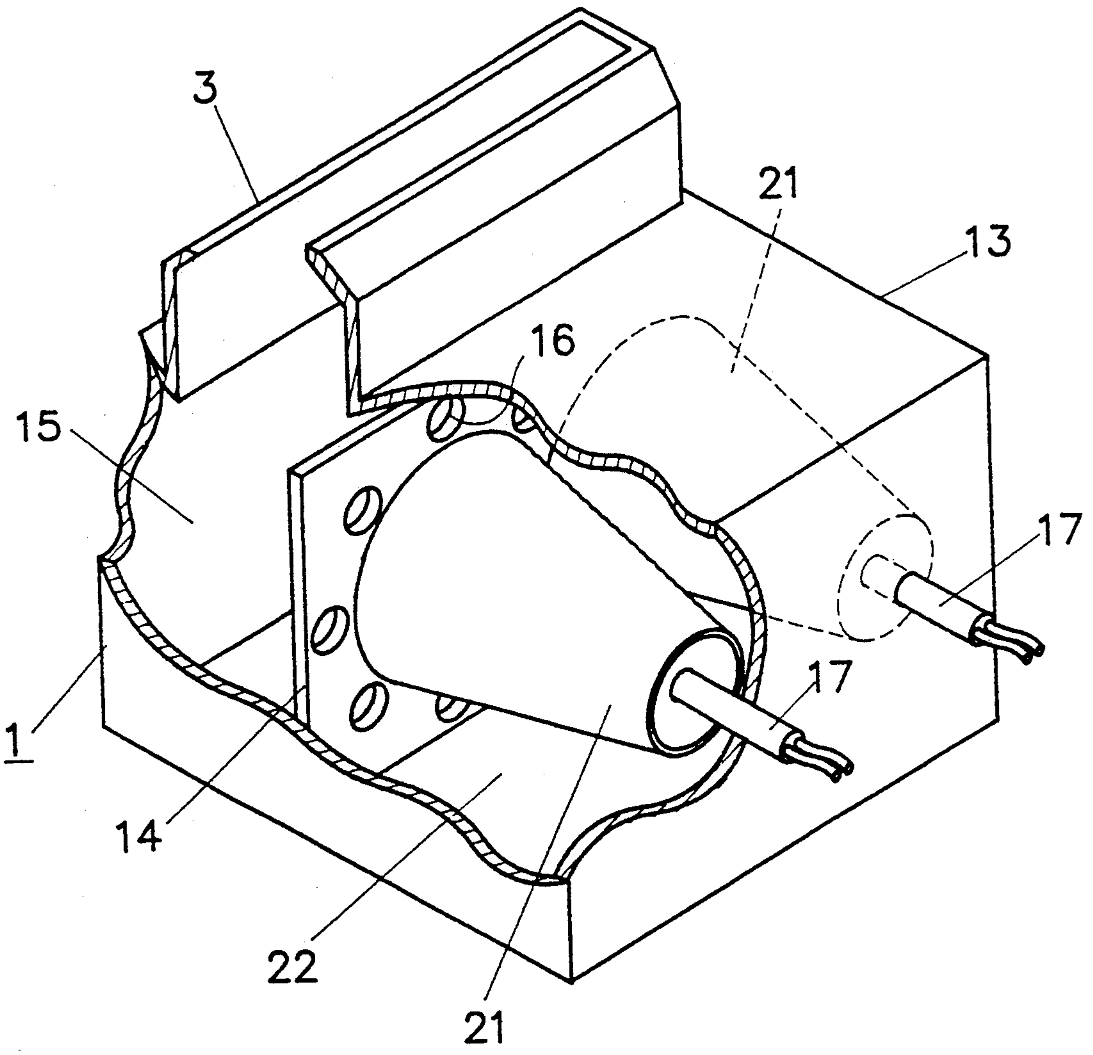
FIG. 3 is a perspective view showing partly cutaway atomizer for forming a thin film according to a second embodiment of the present invention.
Figure 4:
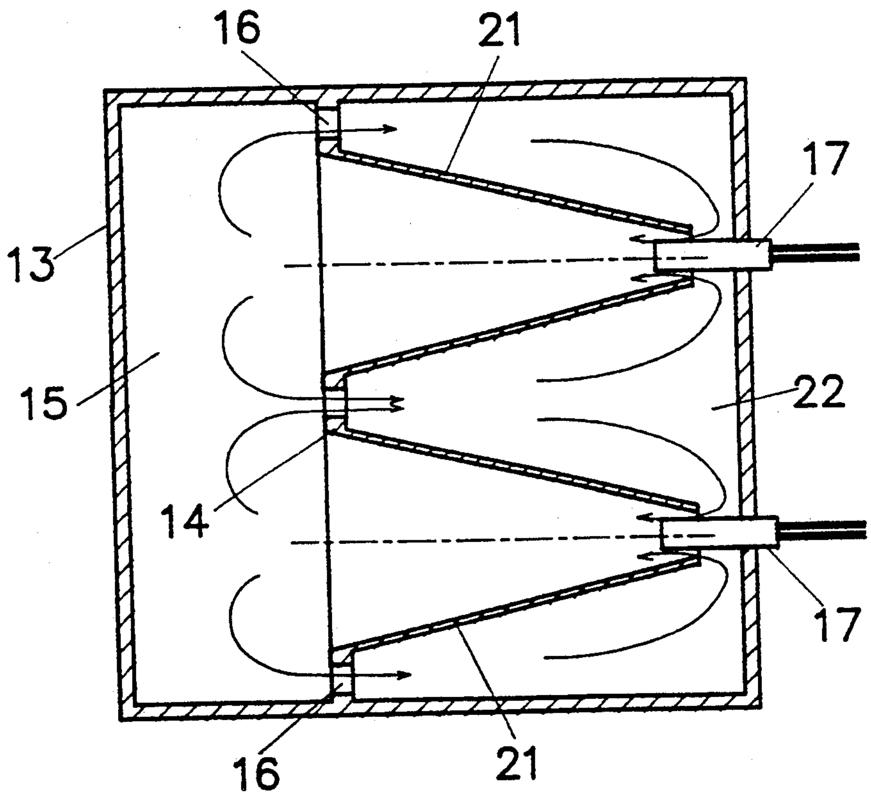
FIG. 4 is a lateral cross sectional plan view of the atomizer for forming a thin film of FIG. 3.

A second embodiment of the atomizer according to the present invention will be described with reference to FIGS. 3 and 4.

A pair of guide tubes 21, 21, respectively provided with nozzles 17, 17, are disposed parallel to each other in the atomizing box 13. Inasmuch as the nozzles 17, 17 are separated from each other by the guide tubes 21, 21, the atomized solutions hardly interfere with each other. Accordingly, a large amount of solution is not sprayed from each nozzle 17 which results in increasing two times the amount of the atomized solution discharged from the atomized solution discharger 3 without spraying a large amount of atomized solution. As a result, it is possible to discharge a large amount of atomizing solution having fine particle per unit time.

THIRD EMBODIMENT (FIGS. 5 AND 6)

Figure 5:
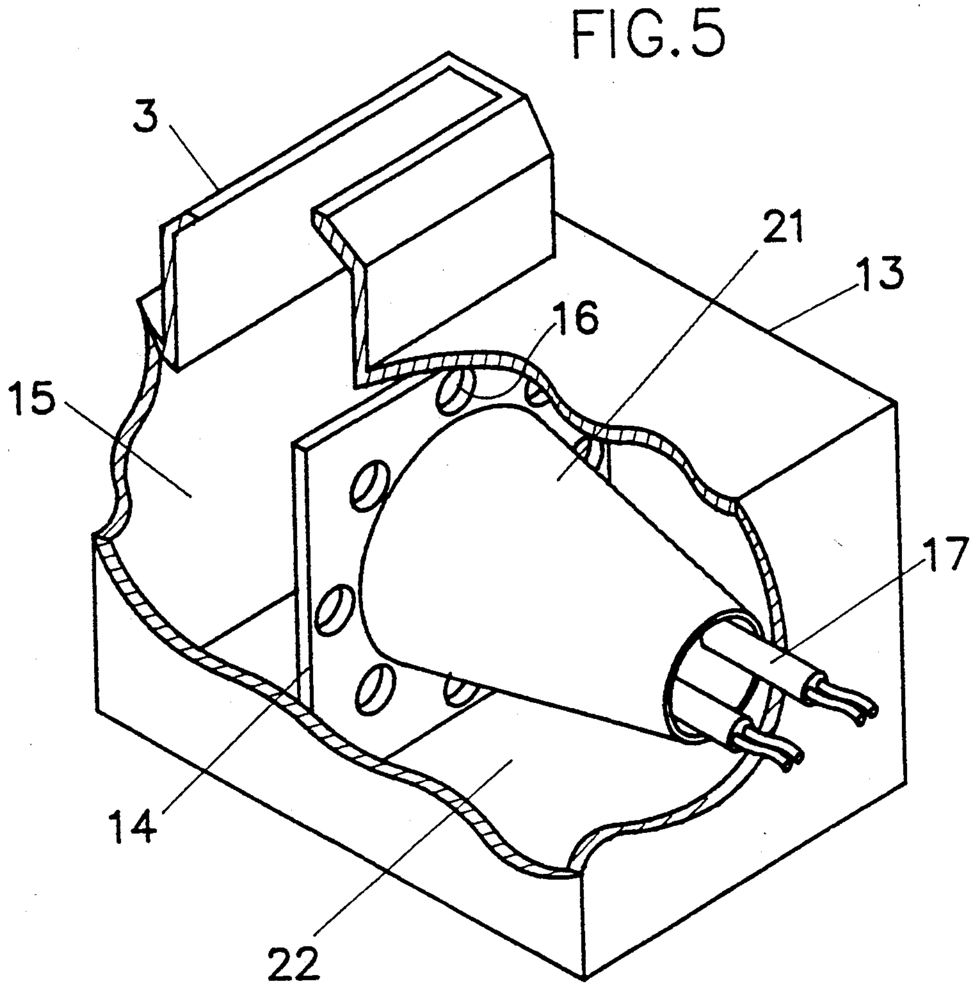
FIG. 5 is a perspective view showing partly cutaway atomizer for forming a thin film according to a third embodiment of the present invention.
Figure 6:
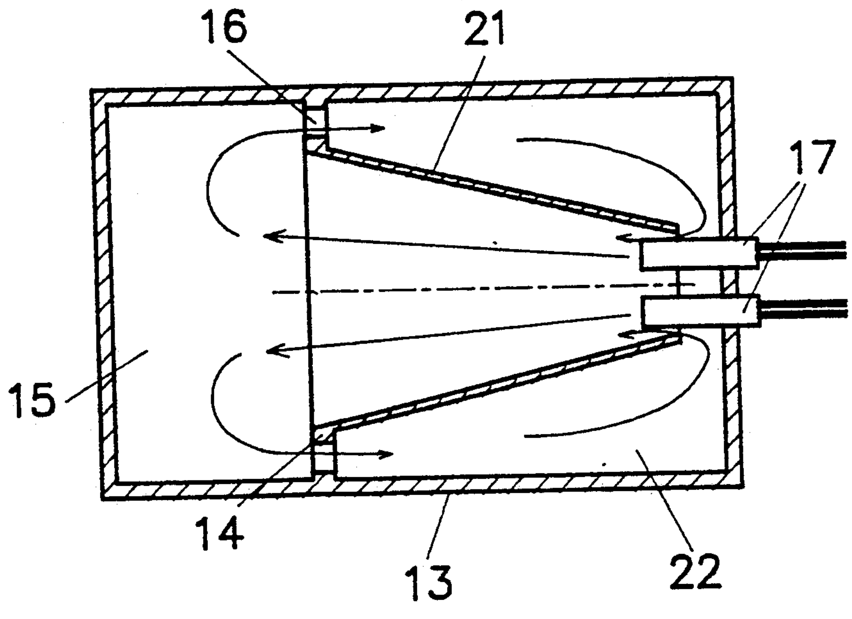
FIG. 6 is a lateral cross sectional plan view of the atomizer of FIG. 5.

A third embodiment of the atomizer according to the present invention will be described with reference to FIGS. 5 and 6.

The guide tube 21 has two nozzles 17, 17 provided at the open or base end thereof. The two nozzles 17, 17 are disposed symmetrically relative to the central axis of the guide tube 21 for thereby spraying the atomizing solution in a direction parallel to the central axis. If the two nozzles 17, 17 are disposed at a position adjacent to each other, the atomized solution sprayed by the nozzles 17, 17 interfere with each other to produce an atomized solution having coarse particles. The atomized solution having coarse particle collides with the wall surface of the guide tube 21 and the wall surface facing the atomizing solution reservoir 15 where the atomized solution having coarse particles is eliminated so that the amount of the atomized solution to be supplied to the film formation chamber is reduced compared with the atomizer of the second embodiment provided with the pair of nozzles 17, 17 as illustrated in FIGS. 3, 4.

It is possible to provide guide tubes 21, 21 respectively having two nozzles 17, 17.

FOURTH EMBODIMENT (FIGS. 8 AND 9)

Figure 8:
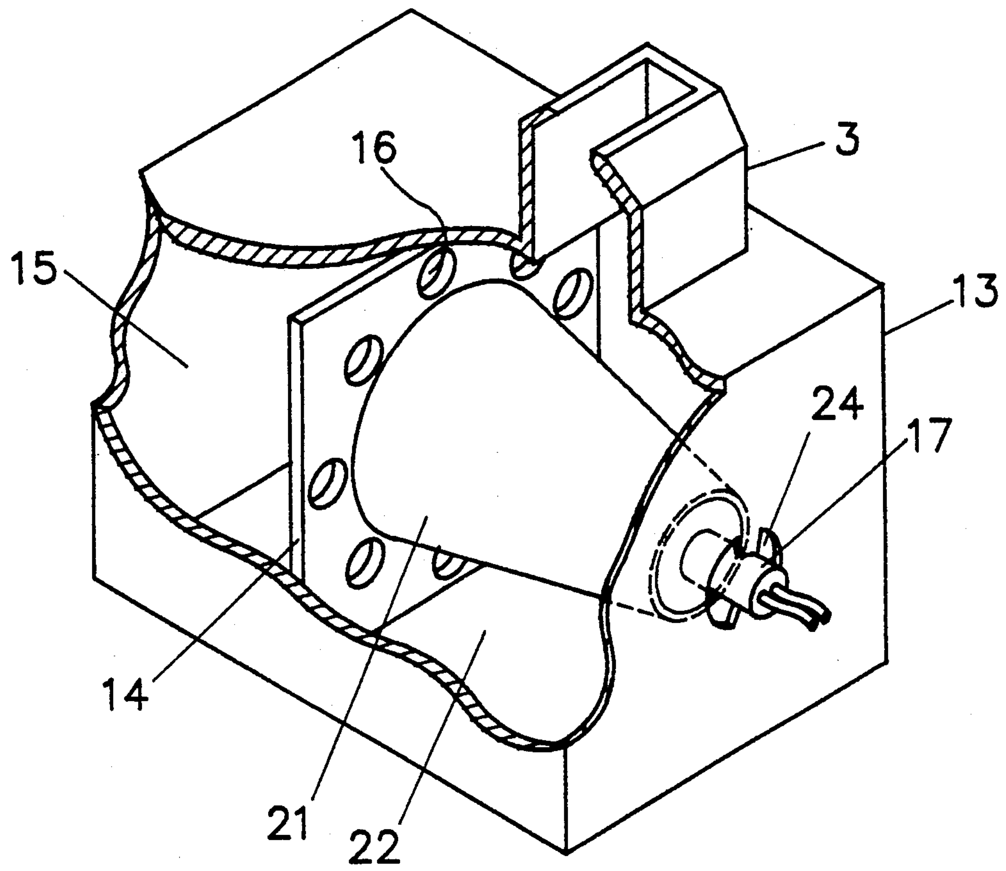
FIG. 8 is a perspective view showing a partially cutaway atomizer according to a fourth embodiment of the present invention.
Figure 9:
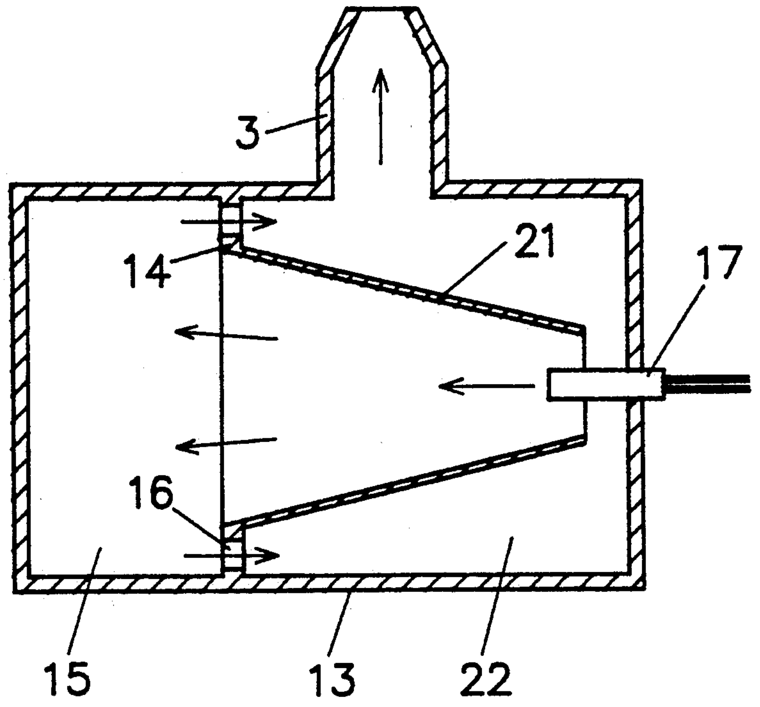
FIG. 9 is a longitudinal cross sectional side view of the atomizer shown in FIG. 8.

A fourth embodiment of the atomizer according to the present invention will be described with reference to FIGS. 8 and 9.

In the fourth embodiment of the atomizer according to the present invention, the structure of the atomizer is identical to that of the first embodiment except that the atomizer solution discharger 3 is provided in the outer wall of the atomizing box 13 defining the return passage 22 with the atomizing guide tube 21.

The higher the pressure of the atomized solution sprayed from the nozzle 17, the larger the quantity of the atomized solution that flows from the reservoir 15 to the return passage 22. The atomized solution flowing into the return passage from the reservoir 15 through the through holes 16 contains fine particles of the atomized solution highly dispersed in air. Therefore, this embodiment provides a highly atomized solution by returning the atomized particles from the reservoir 15 to the return passage 22 and discharging them therefrom.

Although the invention has been described in its preferred form with a certain degree of particularity, it is understood that many variations and changes are possible in the invention without departing from the scope thereof.

What is claimed is:

1. An atomizer for forming a thin film comprising:
an atomizing box;
a partition wall provided in said atomizing box and dividing said atomizing box into an atomizing solution reservoir and a fluid return passage, said partition wall having a plurality of perforations provided therein providing fluid communication between said atomizing solution reservoir and said fluid return passage;
a guide tube having an open end of small diameter and another open end of large diameter, said guide tube being contained within said fluid return passage and having said open end of small diameter provided at a sidewall of said atomizing box and said open end of large diameter provided at said partition wall;
a nozzle having an ejection outlet extending through said sidewall and into said guide tube open end of small diameter so as to spray from the open end of small diameter to the open end of large diameter of the guide tube; and
an atomized solution discharger positioned above and connected to said atomizing solution reservoir.

2. An atomizer for forming a thin film according to claim 1, wherein the atomizing box contains a plurality of said guide tubes, each of said guide tubes being provided with a said nozzle.

3. An atomizer for forming a thin film according to claim 1, wherein the guide tube has a plurality of said nozzles positioned therein.

4. An atomizer for forming a thin film according to claim 1, wherein the fluid return passage extends from the perforations to the open end of small diameter and around the circumference of the guide tube.

5. An atomizer for forming a thin film according to claim 1, wherein the guide tube has an inner diameter which is tapered to increase from the open end of small diameter to the open end of large diameter.

6. An atomizer for forming a thin film according to claim 1, comprising means for providing air fluid and liquid fluid to the nozzle.

7. An atomizer for forming a thin film according to claim 1, comprising means for providing liquid fluid to the nozzle.

8. An atomizer for forming a thin film comprising:
an atomizing box;
a partition wall provided in said atomizing box and dividing said atomizing box into an atomizing solution reservoir and a fluid return passage, said partition wall having a plurality of perforations provided therein providing fluid communication between said atomizing solution reservoir and said fluid return passage;
a guide tube having an open end of small diameter and another open end of large diameter, said guide tube being contained within said fluid return passage and having said open end of small diameter provided at a sidewall of said atomizing box and said open end of large diameter provided at said partition wall;
a nozzle having an ejection outlet extending through said sidewall and into said guide tube open end of small diameter so as to spray from the open end of small diameter to the open end of large diameter of the guide tube; and
an atomized solution discharger positioned above and connected to said fluid return passage.

9. An atomizer for forming a thin film according to claim 8, wherein the fluid return passage extends from the perforations to the open end of small diameter and around the circumference of the guide tube.

10. An atomizer for forming a thin film according to claim 8, wherein the guide tube has an inner diameter which is tapered to increase from the open end of small diameter to the open end of large diameter.

* * * * *